United States Patent
Ni et al.

(10) Patent No.: US 6,174,992 B1
(45) Date of Patent: Jan. 16, 2001

(54) HUMAN ENDOMETRIAL SPECIFIC STEROID-BINDING FACTOR I, II AND III

(75) Inventors: Jian Ni, Rockville; Guo-Liang Yu, Darnestown; Reiner Gentz, Silver Spring, all of MD (US)

(73) Assignee: Human Genome Sciences, Inc., Rockville, MD (US)

( * ) Notice: Under 35 U.S.C. 154(b), the term of this patent shall be extended for 0 days.

(21) Appl. No.: 09/263,810

(22) Filed: Mar. 8, 1999

Related U.S. Application Data

(62) Division of application No. 08/821,451, filed on Mar. 21, 1997.
(60) Provisional application No. 60/014,724, filed on Mar. 21, 1996.

(51) Int. Cl.[7] .................................................. C07K 14/46
(52) U.S. Cl. .............................................................. 530/324
(58) Field of Search .............................................. 530/324

(56) References Cited

FOREIGN PATENT DOCUMENTS

| WO 96/38463 | 12/1996 | (WO) . |
|---|---|---|
| 9807857 | 2/1998 | (WO) . |
| 9821331 | 5/1998 | (WO) . |
| WO 98/35229 | 8/1998 | (WO) . |
| WO 98/56248 | 12/1998 | (WO) . |
| WO 99/19487 | 4/1999 | (WO) . |

OTHER PUBLICATIONS

Supplemental European Search Report, Application No. 96910504.8.
Watson et al. (1996) Cancer Research 56:860–865.
Peri et al. J. (1993) J. Clinical Investigation 92:2099–2109.
Peri et al. (1995) J. Clinical Investigation 96:343–353.
Bernard et al. (1992) Clinica Chimica Acta. 207:239–249.
Hay et al. (1995) Am. Physiol. 268:L565–L575.
Jensen et al. (1994) Int. J. Cancer 58:629–637.
Wolf et al. (1992) Human Molecular Genetics 1(6):371–378.
Okutani et al. (1992) J. Chromatography 577:25–35.
Singh et al., (1988) Biochim. Biophys. Acta 950:329–337.
George et al. (1988) Current Methods in Sequence Comparison & Analysis, pp. 127–149.
Miele et al. (1994) J. Endocrinol. Invest. 17:679–692.
Peri et al. (1994) DNA and Cell Biol. 13(5):495–503.
Miele et al. (1988) Nature 335:726–730.

*Primary Examiner*—Charles L. Patterson, Jr.
(74) *Attorney, Agent, or Firm*—Human Genome Sciences Inc.

(57) ABSTRACT

The invention relates to hESF I, II and III polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

96 Claims, 6 Drawing Sheets

```
        10                  30                  50
TCACTCATTGTGAAAGCTGAGCTCACAGCCGAATAAGCCACCATGAGGCTGTCAGTGTGT
                                              M  R  L  S  V  C
        70                  90                 110
CTCCTGATGGTCTCGCTGGCCCTTTGCTGCTACCAGGCCCATGCTCTTGTCTGCCCAGCT
 L  L  M  V  S  L  A  L  C  C  Y  Q  A  H  A  L  V  C  P  A
       130                 150                 170
GTTGCTTCTGAGATCACAGTCTTCTTATTCTTAAGTGACGCTGCCGTAAACCTCCAAGTT
 V  A  S  E  I  T  V  F  L  F  L  S  D  A  A  V  N  L  Q  V
       190                 210                 230
GCCAAACTTAATCCACCTCCAGAAGCTCTTGCAGCCAAGTTGGAAGTGAAGCACTGCACC
 A  K  L  N  P  P  P  E  A  L  A  A  K  L  E  V  K  H  C  T
       250                 270                 290
GATCAGATATCTTTTAAGAAACGACTCTCATTGGAAAAAGTCCTGGTGGAAATAGTGAAA
 D  Q  I  S  F  K  K  R  L  S  L  E  K  V  L  V  E  I  V  K
       310                 330                 350
AAATGTGGTGTGTGACATGTAAAAATGCTCAACCTGGTTTCCAAAGTCTTTCAACGACAC
 K  C  G  V
       370                 390                 410
CCTGATCTTCACTAAAAATTGTAAAGGTTTCAACACGTTGCTTTAATAAATCACTTGCCC
       430
TGCACATCAAAAA           FIG.1
```

```
        10                  30                  50
TTGTTTGTGAAAGCTGAGCTCACAGCAAAACAAGCCACCATGAAGCTGTCGGTGTGTCTC
                                            M  K  L  S  V  C  L
        70                  90                 110
CTGCTGGTCACGCTGGCCCTCTGCTGCTACCAGGCCAATGCCGAGTTCTGCCCAGCTCTT
 L  L  V  T  L  A  L  C  C  Y  Q  A  N  A  E  F  C  P  A  L
       130                 150                 170
GTTTCTGAGCTGTTAGACTTCTTCTTCATTAGTGAACCTCTGTTCAAGTTAAGTCTTGCC
 V  S  E  L  L  D  F  F  F  I  S  E  P  L  F  K  L  S  L  A
       190                 210                 230
AAATTTGATGCCCCTCCGGAAGCTGTTGCAGCCAAGTTAGGAGTGAAGAGATGCACGGAT
 K  F  D  A  P  P  E  A  V  A  A  K  L  G  V  K  R  C  T  D
       250                 270                 290
CAGATGTCCCTTCAGAAACGAAGCCTCATTGCGGAAGTCCTGGTGAAAATATTGAAGAAA
 Q  M  S  L  Q  K  R  S  L  I  A  E  V  L  V  K  I  L  K  K
       310                 330                 350
TGTAGTGTGTGACATGTAAAAACTTTCATCCTGGTTTCCACTGTCTTTCAATGACACCCT
 C  S  V
       370                 390                 410
GATCTTCACTGCAGAATGTAAAGGTTTCAACGTCTTGCTTTAATAAATCACTTGCTCTCC
       430
AAAAAAAAAAAAAAAA        FIG.2
```

```
                10                     30                    50
    ACGAGCTGCCACGCACGACTGAACACAGACAGCAGCCGCCTCGCCATGAAGCTGCTGATG
                                                    M  K  L  M
                70                     90                   110
    GTCCTCATGCTGGCGGCCCTCCTCCTGCACTGCTATGCAGATTCTGGCTGCAAACTCCTG
    V  L  M  L  A  A  L  L  L  H  C  Y  A  D  S  G  C  K  L  L
               130                    150                   170
    GAGGACATGGTTGAAAAGACCATCAATTCCGACATATCTATACCTGAATACAAAGAGCTT
    E  D  M  V  E  K  T  I  N  S  D  I  S  I  P  E  Y  K  E  L
               190                    210                   230
    CTTCAAGAGTTCATAGACAGTGATGCCGCTGCAGAGGCTATGGGGAAATTCAAGCAGTGT
    L  Q  E  F  I  D  S  D  A  A  A  E  A  M  G  K  F  K  Q  C
               250                    270                   290
    TTCCTCAACCAGTCACATAGAACTCTGAAAAACTTTGGACTGATGATGCATACAGTGTAC
    F  L  N  Q  S  H  R  T  L  K  N  F  G  L  M  M  H  T  V  Y
               310                    330                   350
    GACAGCATTTGGTGTAATATGAAGAGTAATTAACTTTACCCAAGGCGTTTGGCTCAGAGG
    D  S  I  W  C  N  M  K  S  N  *
               370                    390                   410
    GCTACAGACTATGGCCAGAACTCATCTGTTGATTGCTAGAAACCACTTTCTTCTTGTGTT
               430                    450                   470
    GCTTTTTATGTGGGAACTGCTAGACAACTGTTGAAACCTCAATTCATTCCATTTCA
```

FIG.3

```
 1 MRLSVCLLMVSLALCCYQAHA.LVCPAVASEITVFLFLSDAAVNLQVAKL 49
   : ||:|||:: ||:|||:|:|  :|. || |.. ||: |:...:. ::...
 4 ielslcllim.lavccyeanasqicelvahetisflmkseeelkkelemy 52

50 NPPPEALAAKLEVKHCTDQISFKKRLSLEKVLVEIVKKCGV 90
   |:||.|:..||||||:|.||:|  .|| :...|| |. .|||
53 nappaaveaklevkrcvdqmsngdrlvvaetlvyiflecgv 93
```

FIG.4

```
  1 MKLSVCLLLVTLALCCYQANA.EFCPALVSELLDFFFISEPLFKLSLAKF 49
    :.||:|||::  ||:|||:|||  ::|. :. |  :.|:: ||. :| .|..:
  4 ielslcllim.lavccyeanasqicelvahetisflmkseeelkkelemy 52

50 DAPPEAVAAKLGVKRCTDQMSLQKRSLIAEVLVKILKKCSV 90
    :|||.||.|||:||||.||||  ..|  ::||.|| |: .|:|
 53 nappaaveaklevkrcvdqmsngdrlvvaetlvyiflecgv 93
```

FIG.5

```
  1 MKLLMVLMLAALLLHCYA.DSGCKLLEDMVEKTINSDISIPEYKELLQEF 49
    |||:::::|..: :  ||| :|||.:|::::  ||||.:.:.:|..|:..:
  1 mklvflfllvtipiccyasgsgcsildevirgtinstvtlhdymklvkpy 50

50 IDSDAAAEAMGKFKQCFLNQSHRTLKNFGLMMHTVYDSIWCNMKSN 95
    ::..  ...|: .||||||:|..:||.|.|:||..:::| .|. .|
 51 vgahftekavkqfkqcfldqtdktlenvgvmmeaifnsescqqps. 95
```

FIG.6

HUMAN ENDOMETRIAL SPECIFIC STEROID-BINDING FACTOR I, II AND III

This application claims priority to application Ser. No. 08/821,451, filed Mar. 21, 1997, and Provisional application Ser. No. 06/014,724, filed Mar. 21, 1996, both herein incorporated by reference in their entirety.

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human endometrial specific steroid-binding factor I, II and III, sometimes hereinafter referred to as "hESF I, II and III".

BACKGROUND OF THE INVENTION

The regulation of cells and tissues is controlled by autocrine and paracrine factors, such as systemic hormones and factors that modulate or mediate the action of hormones.

Many peptides, expressed locally, can influence certain biological activity in the mammalian system and are very important in the regulation of cells of the epithelium. These factors largely have not been identified or characterized particularly not in humans.

A few factors that play a role in the regulation of functions of the lung and uterus, both adult and fetal, have been identified in non-human organisms. One such factor is mammalian CC10, i.e., human, rat and rabbit CC10. (Wolf, M. et al., *Human Molecular Genetics*, 1(6):371–378 (1992)). Clara Cell 10 kDa secretory protein (CC10) which is also called Clara Cell 17 kDa protein, is a homodimer consisting of 8.5 kDa monomers that are joined by two disulfide bonds (Umland, T. C. et al., *J. Mol. Biol.*, 224:441–448 (1992)). It is the predominant secreted protein of lung Clara cells which are the lining of the bronchiolar epithelium (Singh, G. and Katyal, S. L., *J. Histochem. Cytochem.*, 32:49–54 (1984)). The physiological role of the protein is not yet completely understood. It has been reported that CC10 specifically binds methylsulfonyl-polychlorated biphenyls (PCBS) (Nordlund, Moler, L. et al., *J. Biol. Chem.*, 265:12690–12693 (1990)) and inhibits phospholipase $A_2$ (Singh, G. et al., *Biochem. Biophys. Acta*, 1039:348–355 (1990)). In the last few years the sequences of rat (Katyal, S. L. et al., *Prog. Respir. Res.*, 25:29–35 (1990); and Hagen, G. et al., *Nucleic Acids Res.*, 18:2939–2946 (1990)), and human (Singh, G. et al., *Biochem. Biophys. Acta*, 950:329–337 (1988) CC10 cDNAs have been reported. cDNAs, and the derived amino acid sequences, show striking homologies to rat uteroglobin (Singh, G. et al., *Biochem. Biophys. Acta*, 1039:348–355 (1990); and Hagen, G. et al., *Nucleic Acids Res.*, 18:2939–2946 (1990)).

Like CC10, rat uteroglobin is a covalently bound homodimer whose three dimensional structure is well known (Morize, I. et al., *J. Mol. Biol.*, 194:725–739 (1987). Uteroglobin expression in rabbits has been originally reported in the uterus during the preimplantation phase (Beier, H. M., *Biochem. Biophys. Acta*, 160:289–290 (1968)). More recently, the protein was also detected in oviduct (Kirchner, C., Cell Tissue Res., 170:490–492 (1976)), male genital organs (Beier, H. M. et al., *Cell Tissue Res.*, 165:1–11 (1975)), esophagus (Noske, I. G. and Feigelson, M., *Biol. Reprod.*, 15:704–713 (1976)) and lung (Noske, supra; and Torkkeli, T. et al., *Biochem. Biophys. Acta*, 544:578–592 (1978)).

In vitro, several distinct properties of uteroglobin have been described. Soon after its discovery it could be shown that the steroid hormone progesterone is specifically bound by the protein (Beato, M. and Baier, R., *Biochem. Biophys. Acta*, 392:346–356 (1975); and Beato, M. et al., *J. Steriod Biochem.*, 8:725–730 (1977)). Therefore, rabbit uteroglobin was believed to be a potential carrier or scavenger of progesterone that regulates the progesterone concentration in the endometrium (Atger, M. et al., *J. Steroid Biochem.*, 13:1157–1162 (1980)). It has also been shown to specifically bind certain methylsulfonyl metabolites of polychlorinated biphenyls with even higher affinity than progesterone (Gillner, M. et al., *J. Steroid Biochem.*, 31:27–33 (1988)). Furthermore, uteroglobin has been found to inhibit phospholipase $A_2$. The relationships of all these properties and their physiological significance is still not understood and remains largely a matter of speculation.

The rat CC10 mRNA is expressed like rat uteroglobin not only in lung but also in the esophagus as well in uteri of estrogen and progesterone treated female rats (Hagen, G. 1990 supra) suggesting that rat CC10 is the rat counterpart of rat uteroglobin (see in general Wolf, M. et al., *Human Molecular Genetics*, 1(6):371–378 (1992)).

Human CC10 expression is abundant in non-neoplastic human lung, and it is detectable in tumors in corresponding cell lines at markedly lower levels (Broers, J. L. V. et al., *Lab. Invest.*, 66:337–346 (1992); Linnoila, R. I. et al., *Amer. J. Clin. Pathol.*, 90:1–12 (1988)). CC10 levels were also significantly lower in serum and bronchoalveolar lavage specimens obtained from smokers and lung cancer patients compared with specimens from healthy non-smokers (Bernard, A. et al., *Europ. Resp. J.*, 5:1231–1238 (1992)).

These findings suggest the expression of CC10 mRNA becomes altered in distinct lung compartments and may implicate a role for CC10 in the development of pulmonary carcinomas (Jensen, S. M. et al., *Int. J. Cancer*, 58:629–637 (1994).

Some of the biological properties of UG, such as masking the antigenicity of blastomers (Mukherjee, A. B., et al., *Med. Hypotheses*, 6:1043–1055 (1980)) and epididymal spermatozoa (Mukherjee, D. C., et al., *Science (Washington D.C.)*, 219:989–991 (1983)), inhibition of monocyte and neutrophil chemotaxis and phagocytosis in vitro (Schiffman, E. V., et al., *Agents Actions Suppl.*, 12:106–120 (1983)), and inhibition of ADP- and thrombin-induced (but not of arachidonic acid-induced) platelet aggregation (Manjunath, R., et al., *Biochem. Pharmacol.*, 36:741–746 (1987)), may be due, at least in part, to the potent inhibitory effect of this protein on $PLA_2$ activity (Levin, S. W., et al., *Life Sci.*, 38:1813–1819 (1986)). A nonapeptide derived from the amino acid sequence of α-helix-3 of UG monomer (residues 39–47) possesses all the biological properties of the intact protein and has been identified as an active site of UG responsible for its $PLA_2$-inhibitory and antiinflammatory activities (Miele, L., et al., *Nature (Lond.)*, 335:726–730 (1988)).

It has been indicated that cc10kD-specific transcripts are present in several nonrespiratory human organs and tissues. By using an antibody to rabbit UG, a UG-like immunoreactivity in human endometrium (Kikukawa, T., et al., *J. Clin. Endocrinol. Metab.*, 67:315–321 (1988)), prostate (Manyak, M. J., et al., *J. Urol.*, 140:176–182 (1988)), and respiratory tract (Dhanireddy, R., et al., *Biochem. Biophys. Res. Commun.*, 152:1447–1454 (1988)), has been described.

Recently, the cDNA (Singh, G., et al., *Biochem. Biophys. Acta,* 950:329–337 (1988)) and the 5' regions (Wolf, M., et al., Human *Mol. Genet.,* 1:371–378 (1992)) of the gene encoding human uteroglobin (hUG), a counterpart of rabbit UG (rUG), has been characterized. Human UG or Clara cell 10-kD protein has 61.5% amino acid sequence identity with rUG (Singh, G., et al., *Biochem. Biophys. Acta,* 950:329–337 (1988)), 54.2% similarity with rat UG (Singh, G., et al., *Biochem. Biophys. Acta,* 1039:348–355 (1990)), and 52.8% with mouse UG (Singh, G., et al., *Exp. Lung Res.,* 19:67–75 (1993)). Although this protein was originally discovered in the alveolar Clara cells (Singh, G., et al., *J. Histochem.,* 36:73–80 (1988)) it is detectable in many extrapulmonary tissues similar to the ones in which rUG is expressed (Peri, A., et al., *DNA Cell Biol.,* 5:495–503 (1994)) and this expression is induced by progesterone. It appear that some of the biological properties of hUG are virtually identical to rUG (Mantile, G., et al., *J. Biol. Chem.,* 27:20343–20351 (3993)).

It has been reported that UG in the rabbit uterine fluid is first detectable on day 3 of pregnancy, and peak level is reached on day 5 (for a review see Miele, L., et al., *Endocr. Rev.,* 8:47414 490 (1987)). UG, by inhibiting $PLA_2$ activity, may down-regulate the production of proinflammatory lipid mediators, which promote contraction and motility of the uterine smooth muscle. Therefore, it is suggested that UG facilitates the maintenance of myometrial quiescence during gestation.

There is a clear need in the art to further isolate and characterize proteins which are homologues of mammalian Clara cell 10 kDa secretory protein and rat prostatic steroid-binding protein. The genes and gene products of the present invention display homology to the rat prostatic steroid-binding protein and Clara cell 10 kDa secretory protein.

SUMMARY OF THE INVENTION

Toward these ends, and others, it is an object of the present invention to provide polypeptides, inter alia, that have been identified as novel hESF I, II and III by homology between the amino acid sequence set out in FIGS. 1, 2 and 3 (SEQ ID NO:2, 4 and 6) and known amino acid sequences of other proteins such as rat prostatic steroid-binding protein.

It is a further object of the invention, moreover, to provide polynucleotides that encode hESF I, II and III, particularly polynucleotides that encode the polypeptides herein designated HESF I, II and III.

In a particularly preferred embodiment of this aspect of the invention the polynucleotides comprise the regions encoding human hESF I, II and III in the sequence set out in FIGS. 1, 2 and 3 (SEQ ID NO:2, 4 and 6).

In accordance with this aspect of the present invention there is provided isolated nucleic acid molecules encoding mature polypeptides expressed by the human cDNA contained in ATCC Deposit No. 97401 (ESF I), 97402 (ESF II) and 97403 (ESF III).

In accordance with this aspect of the invention there are provided isolated nucleic acid molecules encoding human hESF I, II and III, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human hESF I, II and III.

It also is an object of the invention to provide hESF I, II and III polypeptides, particularly human hESF I, II and III polypeptides, that treat and/or prevent inflammation, asthma, rhinitis, cystic fibrosis, airway disease, neoplasia, atopy, inhibit phospholipase $A_2$ activity, bind polychlorinated biphenyls, reduce foreign protein antigenicity, inhibit monocyte and neutrophil chemotaxis and phagocytosis, inhibit platelet aggregation, regulate eicosanoid levels in the human uterus. and control the growth of endometrial cells.

In accordance with this aspect of the invention there are provided novel polypeptides of human origin referred to herein as hESF I, II and III as well as biologically, diagnostically or therapeutically useful fragments, variants and derivatives thereof, variants and derivatives of the fragments, and analogs of the foregoing.

Among the particularly preferred embodiments of this aspect of the invention are variants of human hESF I, II and III encoded by naturally occurring alleles of the human hESF I, II and III genes.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned hESF I, II and III polypeptides comprising culturing host cells having expressibly incorporated therein an exogenously-derived human hESF I, II or III encoding polynucleotide under conditions for expression of human HESF I, II and III in the host and then recovering the expressed polypeptides.

In accordance with another object of the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing hESF I, II and III expression in cells by determining hESF I, II and III polypeptides or HESF I, II and III-encoding MRNA; expressing hESF I, II and III in vitro, ex vivo or in vivo by exposing cells to hESF I, II and III polypeptides or polynucleotides as disclosed herein; assaying genetic variation and aberrations, such as defects, in HESF I, II and III genes; and administering a hESF I, II and III polypeptide or polynucleotide to an organism to augment hESF I, II and III function or remediate hESF I, II and III dysfunction.

In accordance with certain preferred embodiments of this and other aspects of the invention there are provided probes that hybridize to human hESF I, II and III sequences.

In certain additional preferred embodiments of this aspect of the invention there are provided antibodies against hESF I, II and III polypeptides. In certain particularly preferred embodiments in this regard, the antibodies are highly selective for human hESF I, II and III.

In accordance with another aspect of the present invention, ithere are provided hESF I, II and III agonists. Among preferred agonists are molecules that mimic hESF I, II and III, that bind to hESF I, II and III-binding molecules or receptor molecules, and that elicit or augment hESF I, II and III-induced responses. Also among preferred agonists are molecules that interact with hESF I, II and III polypeptides, or with other modulators of hESF I, II and III activities, and thereby potentiate or augment an effect(s) of hESF I, II and III.

In accordance with yet another aspect of the present invention, there are provided hESF I, II and III antagonists. Among preferred antagonists are those which mimic hESF I, II and III so as to bind to hESF I, II and III receptors or binding molecules but not more t a hESF I, II and III-induced response or more than one hESF I, II and III-induced response or which prevent expression of hESF I, II and III. Also among preferred antagonists are molecules that bind to or interact with hESF I, II and III so as to inhibit an effect(s) of hESF I, II and III.

The agonists and antagonists may be used to mimic, augment or inhibit the action of hESF I, II and III polypeptides. They may be used, for instance, to treat and/or prevent an inherited susceptibility to asthma.

In a further aspect of the invention there are provided compositions comprising a hESF I, II or III polynucleotide or a hESF I, II or III polypeptide for administration to cells in vitro, to cells ex vivo and to cells in vivo, or to a multicellular organism. In certain particularly preferred embodiments of this aspect of the invention, the compositions comprise a hESF I, II or III polynucleotide for expression of a hESF I, II or III polypeptide in a host organism for treatment of disease. Particularly preferred in this regard is expression in a human patient for treatment of a dysfunction associated with aberrant endogenous activity.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the nucleotide and deduced amino acid sequence of human hESF I.

FIG. 2 shows the nucleotide and deduced amino acid sequence of human hESF II.

FIG. 3 shows the nucleotide and deduced amino acid sequence of human hESF III.

FIG. 4 shows the regions of similarity between amino acid sequences of hESF I and rat prostatic steroid-binding protein polypeptides (SEQ ID NO:25).

FIG. 5 shows the regions of similarity between amino acid sequences of hESF II and rat prostatic steroid-binding protein polypeptides (SEQ ID NO:26).

FIG. 6 shows the regions of similarity between amino acid sequences of hESF III and rat prostatic steroid-binding protein polypeptides (SEQ ID NO:27).

GLOSSARY

Figure 7:
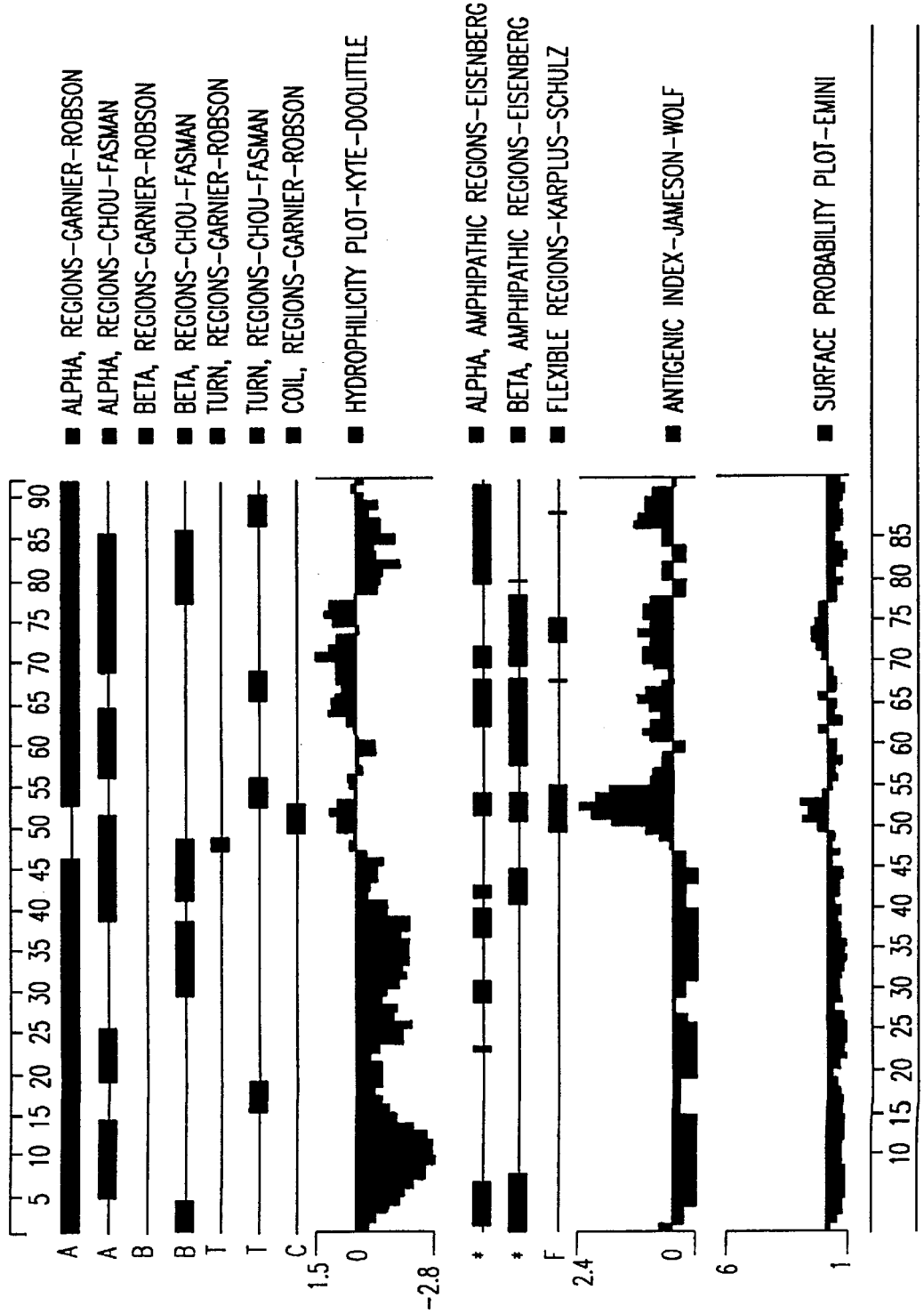
FIG. 7 shows structural and functional features of hESF I deduced by the indicated techniques, as a function of amino acid sequence.
Figure 8:
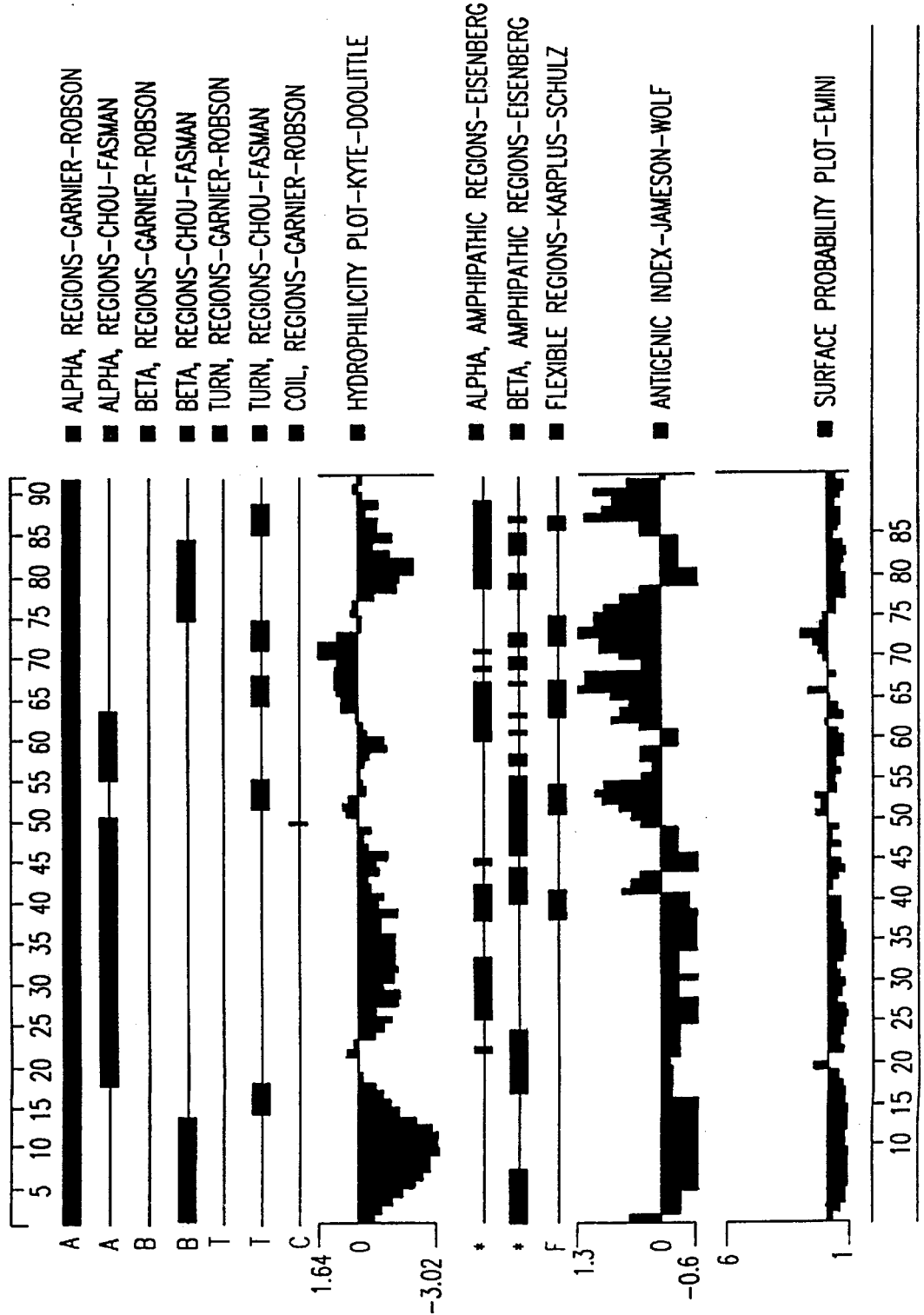
FIG. 8 shows structural and functional features of hESF II deduced by the indicated techniques, as a function of amino acid sequence.
Figure 9:
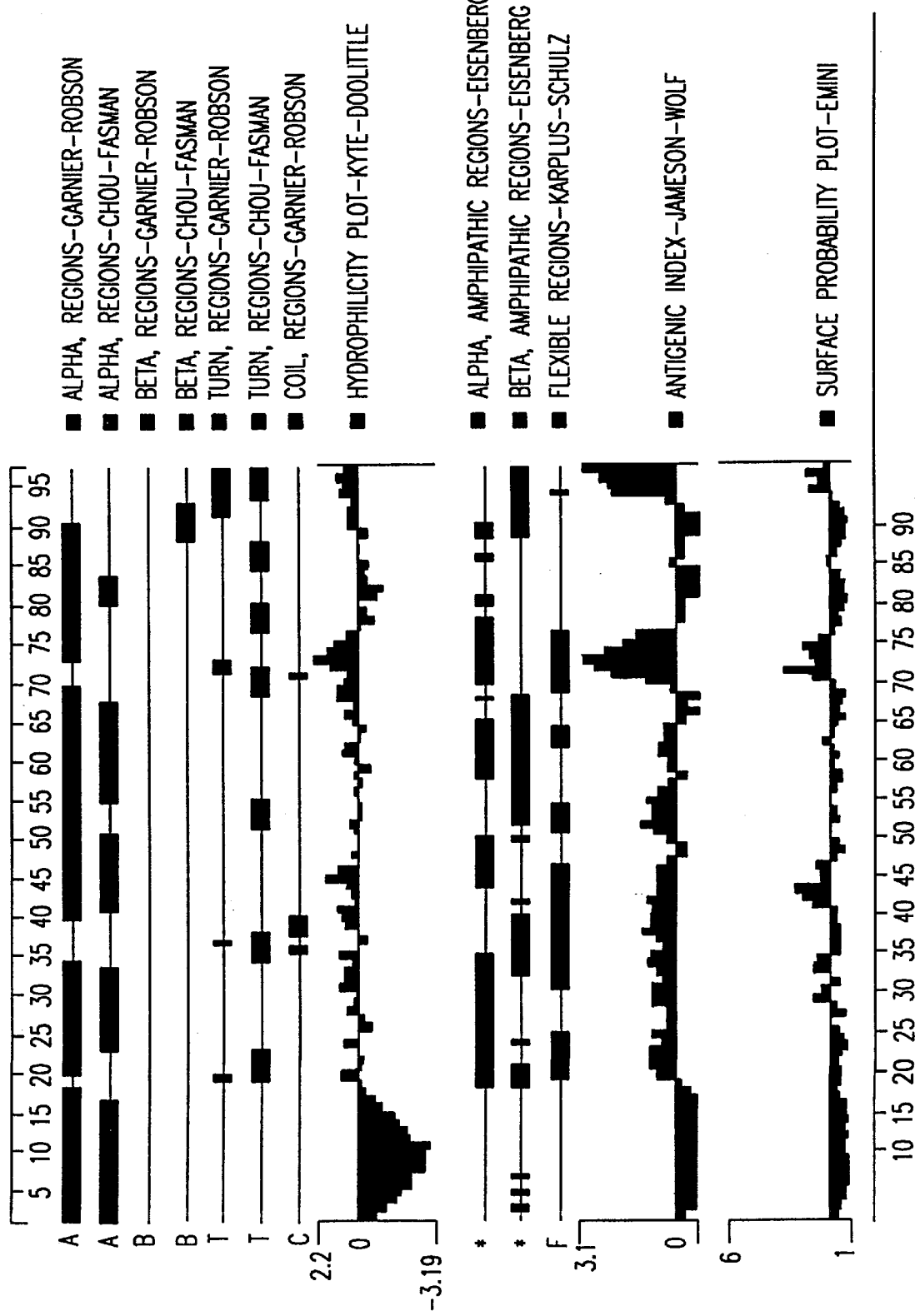
FIG. 9 shows structural and functional features of HESF III deduced by the indicated techniques, as a function of amino acid sequence.

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 µg of plasmid or DNA fragment is digested with about 2 units of enzyme in about 20 µl of reaction buffer. For the purpose of isolating DNA fragments for plasmid construction, typically 5 to 50 µg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a. vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAS, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polyrpeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAS. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

OLIGONUCLEOTIDE (S) refers to relatively short polynucleotides. Often the term refers to single-stranded deoxyribonucleotides, but it can refer as well to single-or double-stranded ribonucleotides, RNA:DNA hybrids and double-stranded DNAS, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. it will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolyticprocessing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with hESF I, II and III polypeptides of the present invention, including not only classic receptors, which are preferred, but also other molecules that specifically bind to or interact with polypeptides of the invention (which also may be referred to as "binding molecules" and "interaction molecules," respectively and as "hESF I, II and III binding molecules" and "hESF I, II and III interaction molecules." Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind to polypeptides of the invention.

Description of the Invention

The present invention relates to novel hESF I, II and III polypeptides and polynucleotides, among other things, as described in greater detail below. In particular, the invention relates to polypeptides and polynucleotides of novel human hESF I, II and III, which are related by amino acid sequence homology to the rat prostatic steroid-binding protein. The invention relates especially to hESF I, II and III having the nucleotide and amino acid sequences set out in FIGS. 1, 2 and 3 (SEQ ID NO:1–6) and to the hESF I, II and III nucleotides and amino acid sequences of the human cDNAs in ATCC Deposit No. 97401, 97402 and 97403 which is herein referred to as "the deposited clone" or as the "cDNA of the deposited clone." It will be appreciated that the nucleotide and amino acid sequences set out in FIGS. 1, 2 and 3 (SEQ ID NO:2, 4 and 6) were obtained by sequencing the cDNA of the deposited clone. Hence, the sequence of the deposited clone is controlling as to any discrepancies between the two and any reference to the sequences of FIGS. 1, 2 and 3 (SEQ ID NO:1, 3 and 5) include reference to the sequence of the human cDNA of the deposited claim.

Polynucleotides

In accordance with one aspect of the present invention, there are provided isolated polynucleotides which encode hESF I, II and III polypeptides having the deduced amino acid sequences of FIGS. 1, 2 and 3 (SEQ ID NO:2, 4 and 6).

Using the information provided herein, such as the polynucleotide sequences set out in FIGS. 1, 2 and 3 (SEQ ID NO:1, 3 and 5) a polynucleotide of the present invention encoding human hESF I, II and III polypeptided may be obtained using standard cloning and screening procedures, such as those for cloning cDNAs using mRNA from cells of a human endometrial tumor as starting material. Illustrative of the invention, the polynucleotide set out in FIG. 1 (SEQ ID NO:1) was discovered in a cDNA library derived from cells of a human endometrial tumor. The polynucleotide of FIG. 2 (SEQ ID NO:3) was discovered in a cDNA library derived from cyclohexamide treated CEM cells. The polynucleotide of FIG. 3 (SEQ ID NO:5) was discovered in a cDNA library derived from human endometrial tumor.

Human hESF I of the invention is structurally related to other proteins of the Clara cell secretory protein family, as shown by the results of sequencing the cDNA encoding human hESF I in the deposited clone. The cDNA sequence thus obtained is set out in FIG. 1 (SEQ ID NO:1). It contains an open reading frame encoding a protein of about 90 amino acid residues, wherein the initial 21 amino acid residues represent a putative leader sequence, with a deduced molecular weight of the full-length protein of about 9.8 kDa. The protein exhibits greatest homology to the rat prostatic steroid-binding protein, among known proteins. The protein hESF I has about 46.067% identity and about 66.3% similarity with the amino acid sequence of the rat prostatic steroid-binding protein.

Human hESF II contains an open reading frame encoding a protein of about 90 amino acid residues, wherein the initial 21 amino acid residues represent a putative leader sequence, with a deduced molecular weight of the full-length protein of about 9.9 kDa. The protein exhibits greatest homology to the rat prostatic steroid-binding protein, among known proteins. The protein hESF II has about 49.438% identity and about 71.910% similarity with the amino acid sequence of rat prostatic steroid-binding protein C2.

Human hESF III contains an open reading frame encoding a protein of about 95 amino acid residues, wherein the initial 21 amino acid residues represent a putative leader sequence, with a deduced molecular weight of the full-length protein of about 8.10 kDa. The protein exhibits greatest homology to rat prostatic steroid-binding protein C3, among known proteins. The protein hESF III has about 36.2% identity and about 64.9% similarity with the amino acid sequence of the rat prostatic steroid-binding protein C3.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptides may be identical to the coding sequence of the polynucleotides shown in FIGS. 1, 2 and 3 (SEQ ID NO:1, 3 and 5). It also may be a polynucleotide with a different sequence, which, as a result of the redundancy (degeneracy) of the genetic code, encodes the polypeptides of the human cDNA of FIGS. 1, 2 and 3 (SEQ ID NO:1, 3 and 5).

Polynucleotides of the present invention which encode the polypeptides of FIGS. 1, 2 and 3 (SEQ ID NO:1, 3 and 5) may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc., among others, many of which are commercially available. As described in Gentz et al., Proc. Natl. Acad. Sci., USA 86: 821–824 (1989), for instance, hexa-histidine provides for convenient purification of the fusion protein. The HA tag corresponds to an epitope derived of influenza hemagglutinin protein, which has been described by Wilson et al., Cell 37: 767 (1984), for instance.

In accordance with the foregoing, the term "polynucleotide encoding a polypeptide" as used herein encompasses polynucleotides which include a sequence encoding a polypeptide of the present invention, particularly human hESF I, II and III having the amino acid sequences set out in FIGS. 1, 2 and 3 (SEQ ID NO:2, 4 and 6). The term encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptides having the deduced amino acid sequences of FIGS. 1, 2 and 3 (SEQ ID NO:2, 4 and 6). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of HESF I, II and III set out in FIGS. 1, 2 and 3 (SEQ ID NO:2, 4 and 6); variants, analogs, derivatives and fragments thereof, and fragments of the variants, analogs and derivatives.

Further particularly preferred in this regard are polynucleotides encoding hESF I, II and III variants, analogs, derivatives and fragments, and variants, analogs and derivatives of the fragments, which have the amino acid sequence of the hESF I, II or III polypeptides of FIGS. 1, 2 and 3 (SEQ ID NO:2, 4 and 6) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the hESF I, II and III. Also especially preferred in this regard are conservative substitutions. Most highly preferred are polynucleotides encoding polypeptides having the amino acid sequences of FIGS. 1, 2 and 3 (SEQ ID NO:2, 4 and 6), without substitutions.

Further preferred embodiments of the invention are polynucleotides that are at least 70% identical to a polynucleotides encoding the hESF I, II and III polypeptides having the amino acid sequences set out in FIGS. 1, 2 and 3 (SEQ ID NO:2, 4 and 6), and polynucleotides which are complementary to such polynucleotides. Alternatively, most highly preferred are polynucleotides that comprise a region that is at least 80% identical to a polynucleotide encoding the hESF I, II or III polypeptides of the cDNA of the deposited clone and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the human cDNA of FIGS. 1, 2 and 3 (SEQ ID NO:1, 3 and 5).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding hESF I, II or III and to isolate cDNA and genomic clones of other genes that have a high sequence similarity to the human hESF I, II or III genes. Such probes generally will comprise at least 15 bases. Preferably, such probes will have at least 30 bases and may have at least 50 bases.

For example, the coding region of the hESF I, II and III genes may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate/protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited materials

A deposit containing a human hESF I, II and III cDNA has been deposited with the American Type Culture Collection, as noted above. Also as noted above, the cDNA deposit is referred to herein as "the deposited clone" or as "the cDNA of the deposited clone."

The deposited clone was deposited with the American Type Culture Collection, 10801 University Boulevard, Manassa, Va. 20110-2209, USA, on Jan. 2, 1996 and assigned ATCC Deposit No. 97401, 97402 and 97403.

The deposited materials are pBluescript SK (−) plasmids (Stratagene, La Jolla, Calif.) containing the full length hESF I, II and III cDNA.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a human hESF I, II and III polypeptide which has the deduced amino acid sequence of FIGS. 1, 2 and 3 (SEQ ID NO:2, 4 and 6).

The invention also relates to fragments, analogs and derivatives of these polypeptides. The terms "fragment,"

"derivative" and "analog" when referring to the polypeptide of FIGS. 1, 2 and 3 (SEQ ID NO:2, 4 and 6) means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIGS. 1, 2 and 3 (SEQ ID NO:2, 4 and 6) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 75% similarity (preferably at least 75% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polsecond polypeptisequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of hESF I, II and III, most particularly fragments of the hESF I, II and III having the amino acid sequence set out in FIGS. 1, 2 and 3 (SEQ ID NO:2, 4 and 6), and fragments of variants and derivatives of the hESF I, II and III of FIGS. 1, 2 and 3 (SEQ ID NO:2, 4 and 6).

In this regard a fragment is a polypeptide having an amino acid sequence that entirely is the same as part but not all of the amino acid sequence of the aforementioned hESF I, II and III polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a hESF I, II or III polypeptide of the present comprised within a precursor polypeptide designed for expression in a host and having heterologous pre and pro-polypeptide regions fused to the amino terminus of the hESF I, II and III fragment and an additional region fused to the carboxyl terminus of the fragment. Therefore, fragments in one aspect of the meaning intended herein, refers to the portion or portions of a fusion polypeptide or fusion protein derived from hESF I, II and III.

As representative examples of polypeptide fragments of the invention, there may be mentioned those which have from about 15 to about 139 amino acids.

In this context about includes the particularly recited range and ranges larger or smaller by several, a few, 5, 4, 3, 2 or 1 amino acid at either extreme or at both extremes. Highly preferred in this regard are the recited ranges plus or minus as many as 5 amino acids at either or at both extremes. Particularly highly preferred are the recited ranges plus or minus as many as 3 amino acids at either or at both the recited extremes. Especially preferred are ranges plus or minus 1 amino acid at either or at both extremes or the recited ranges with no additions or deletions. Most highly preferred of all in this regard are fragments from about 15 to about 45 amino acids.

Among especially preferred fragments of the invention are truncation mutants of hESF I, II and III. Truncation mutants include hESF I, II and III polypeptides having the amino acid sequence of FIGS. 1, 2 and 3 (SEQ ID NO:2, 4 and 6), or variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of hESF I, II and III. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of hESF I, II and III.

Certain preferred regions in these regards are set out in FIGS. 4, 5 and 6 and include, but are not limited to, regions of the aforementioned types identified by analysis of the amino acid sequence set out in FIGS. 1, 2 and 3 (SEQ ID NO:2, 4 and 6). As set out in FIGS. 4, 5 and 6 such preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Among highly preferred fragments in this regard are those that comprise regions of hESF I, II and III that combine several structural features, such as several of the features set out above. In this regard, the regions defined by the residues of FIGS. 1, 2 and 3 (SEQ ID NO:2, 4 and 6), which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of HESF I, II and III. Most highly preferred in this regard are fragments that have a chemical, biological or other activity of hESF I, II and III, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIGS. 4, 5 and 6 (SEQ ID NO:2, 4 and 6) and which include rat prostatic specific-binding proteins. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, host cells, expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art Such techniques are reviewed at length in Sambrook et al. cited above, which is illustrative of the many laboratory manuals that detail these techniques. I n accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* laci and lacZ and promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trpl gene of S. cerevisiae.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include Escherischia coli, Bacillus subtilis and Salmonella typhimurium. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., Cell 23: 175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The hESF I, II and III polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

hESF I, II and III polynucleotides and polypeptides may be used in accordance with the present invention for a variety of applications, particularly those that make use of the chemical and biological properties hESF I, II and III. Additional applications relate to diagnosis and to treatment of disorders of cells, tissues and organisms. These aspects of the invention are illustrated further by the following discussion.

Polynucleotide assays

This invention is also related to the use of the hESF I, II and III polynucleotides to detect complementary polynucleotides such as, for example, as a diagnostic reagent. Detection of a mutated form of hESF I, II and III associated with a dysfunction will provide a diagnostic tool that can add or define a diagnosis of a disease or susceptibility to a disease which results from under-expression, over-expression or altered expression of hESF I, II and III, such as, for example, a susceptibility to inherited asthma and endometrial cancer.

Individuals carrying mutations in the human hESF I, II and III gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., Nature, 324: 163–166 (1986)). RNA or cDNA may also be used in the same ways. As an example, PCR primers complementary to the nucleic acid encoding hESF I, II and III can be used to identify and analyze hESF I, II and III expression and mutations. For example, deletions and insertions can be detected by a change in size of the amplified product in comparison to the normal genotype. Point mutations can be identified by hybridizing amplified DNA to radiolabeled hESF I, II and III RNA or alternatively, radiolabeled hESF I, II and III antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Chromosome assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a hESF I, II and III gene. This can be accomplished using a variety of well known techniques and libraries, which generally are available commercially. The genomic DNA the is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide assays

The present invention also relates to a diagnostic assays such as quantitative and diagnostic assays for detecting levels of hESF I, II and III protein in cells and tissues, and biological fluids such, for example, as blood and urine, including determination of normal and abnormal levels. Thus, for instance, a diagnostic assay in accordance with the invention for detecting over-expression or under-expression of hESF I, II and III protein compared to normal control tissue samples may be used to detect the presence of neoplasia, for example. Assay techniques that can be used to determine levels of a protein, such as an hESF I, II and III protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to hESF I, II or III, preferably a monoclonal antibody. In addition a reporter antibody generally is prepared which binds to the monoclonal antibody. The reporter antibody is attached a detectable reagent such as radioactive, fluorescent or enzymatic reagent, for example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any hESF I, II or III proteins attached to the polystyrene dish. Unbound monoclonal antibody is washed out with buffer. The reporter antibody linked to horseradish peroxidase is placed in the dish resulting in binding of the reporter antibody to any monoclonal antibody bound to hESF I, II or III. Unattached reporter antibody is then washed out. Reagents for peroxidase activity, including a calorimetric substrate are then added to the dish. Immobilized peroxidase, linked to hESF I, II or III through the primary and secondary antibodies, produces a colored reaction product. The amount of color developed in a given time period indicates the amount of hESF I, II or III protein present in the sample. Quantitative results typically are obtained by reference to a standard curve.

A competition assay may be employed wherein antibodies specific to hESF I, II or III attached to a solid support and labeled hESF I, II or III and a sample derived from the host are passed over the solid support and the amount of label detected attached to the solid support can be correlated to a quantity of hESF I, II or III in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal provides antibodieshnique which provides antibodies produced by continuous cell line cultures can be used. Examples include the hybridoma technique (Kohler, G. and Milstein, C., Nature 256: 495–497 (1975), the trioma technique, the human B-cell hybridoma technique (Kozbor et al., Immunology Today 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromotography.

Thus, among others, the polynucleotides and polypeptides of the present invention may be employed to prevent and/or treat inflammation, asthma, rhinitis, cystic fibrosis, airway disease, prevent and/or treat neoplasia, atopy, inhibit phospholipase A$_2$, bind polychlorated biphenyls, reduce foreign protein antigenicity, inhibit monocyte and neutrophil chemotaxis and phagocytosis, inhibit platelet aggregation, regulate eicosanoid levels in the human uterus, control the growth of endometrial cells.

hESF I, II and III binding molecules and assays

This invention also provides a method for identification of molecules, such as receptor molecules, that bind hESF I, II and III. Genes encoding proteins that bind hESF I, II and III, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell responsive to hESF I, II and III, a cDNA library is created from this RNA, the library is divided into pools and the pools are transfected individually into cells that are not responsive to hESF I, II and III. The transfected cells then are exposed to labeled hESF I, II and III. (hESF I, II and III can be labeled by a variety of well-known techniques including standard methods of radio-iodination or inclusion of a recognition site for a site-specific protein kinase.) Following exposure, the cells are fixed and binding of cytostatin is determined. These procedures conveniently are carried out on glass slides.

Pools are identified of cDNA that produced hESF I, II and III-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess hESF I, II and III binding capacity of hESF I, II and III binding molecules, such as receptor molecules, in cells or in cell-free preparations.

Agonists and antagonists - assays and molecules The invention also provides a method of screening compounds to identify those which enhance or block the action of hESF I, II and III on cells, such as its interaction with hESF I, II and III-binding molecules such as receptor molecules. An agonist is a compound which increases the natural biological functions of hESF I, II and III or which functions in a manner similar to hESF I, II and III, while antagonists decrease or eliminate such functions.

For example, a cellular compartment, such as a membrane or a preparation thereof, such as a membrane-preparation, may be prepared from a cell that expresses a molecule that binds hESF I, II and III, such as a molecule of a signaling or regulatory pathway modulated by hESF I, II and III. The preparation is incubated with labeled hESF I, II and III in the absence or the presence of a candidate molecule which may be a hESF I, II and III agonist or antagonist. The ability of the candidate molecule to bind the binding molecule is reflected in decreased binding of the labeled ligand. Molecules which bind gratuitously, i.e., without inducing the effects of HESF I, II and III on binding the hESF I, II and III binding molecule, are most likely to be good antagonists. Molecules that bind well and elicit effects that are the same as or closely related to hESF I, II and III are agonists. hESF I, II and III-like effects of potential agonists and antagonists may by measured, for instance, by determining activity of a second messenger system following interaction of the candidate molecule with a cell or appropriate cell preparation, and comparing the effect with that of hESF I, II and III or molecules that elicit the same effects as hESF I, II and III. Second messenger systems that may be useful in this regard include but are not limited to AMP guanylate cyclase, ion channel or phosphoinositide hydrolysis second messenger systems.

Another example of an assay for hESF I, II and III antagonists is a competitive assay that combines hESF I, II and III and a potential antagonist with membrane-bound hESF I, II and III receptor molecules or recombinant hESF I, II and III receptor molecules under appropriate conditions for a competitive inhibition assay. hESF I, II and III can be labeled, such as by radioactivity, such that the number of hESF I, II and III molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing hESF I, II and III-induced activities, thereby preventing the action of hESF I, II and III by excluding hESF I, II and III from binding.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); OLIGODEOXY-NUCLEOTIDES AS ANTISENSE INHIBITORS OF GENE EXPRESSION, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of hESF I, II and III. The antisense RNA oligonucleotide hybridizes to the mRNA in vivo and blocks translation of the mRNA molecule into hESF I, II and III polypeptide. The oligonucleotides described above can also be delivered to cells such that the antisense RNA or DNA may be expressed in vivo to inhibit production of hESF I, II and III.

The antagonists may be employed in a composition with a pharmaceutically acceptable carrier, e.g., as hereinafter described.

The antagonists may be employed for instance to treat an inherited susceptibility to asthma.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 µg/kg body weight. In most cases they will be administered in an amount not in excess of about 8 µg/kg body weight per day. Preferably, in most cases, dose is from about 10 µg/kg to about 2 µg/kg body weight, daily. It will be appreciated that optimum dosage will be determined by standard methods for each treatment modality and indication, taking into account the indication, its severity, route of administration, complicating conditions and the like.

Gene therapy

The hESF I, II and III polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, YCRE, YCRIP, GP+E-86, GP+envAm12, and DAN cell lines as described in Miller, A., Human Gene Therapy 1: 5–14 (1990). The vector may be transduced into the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook and numerous other references such as, for instance, by Goeddel et al., Nucleic Acids Res. 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 µg of DNA.

Example 1
Expression and Purification of Human hESF I, II and III using Bacteria The DNA sequence encoding human hESP I, II or III in the deposited polynucleotide was amplified using PCR oligonucleotide primers specific to the amino acid carboxyl terminal sequence of the human hESF I, II or III protein and to vector sequences 3' to the gene. Additional nucleotides containing restriction sites to facilitate cloning were added to the 5' and 3' sequences respectively.

The 5' oligonucleotide primer had the sequence for hESF I: 5'CGCGCATGCTTGTCTGCCCAGCTG 3' (SEQ ID NO:7) containing the underlined Sph I restriction site, which encodes a start AUG, followed by 15 nucleotides of the human hESF I coding sequence set out in FIG. 1 (SEQ ID NO:1), beginning with the first base of the codon for amino acid 22 (leucine). for hESF II: 5'CGCCCATGGAGTTCTGCCCAGCTC 3' (SEQ ID NO:8) containing the underlined NcoI restriction site, which encodes a start ATG, followed by 16 nucleotides of the human hESF II coding sequence set out in FIG. 2 (SEQ ID NO:3), beginning with the first base of the codon for amino acid 22.

for hESF III: 5'CGC GCA TGC ACT GCT ATG CAG ATT 3' (SEQ ID NO:9) containing the underlined SphI restriction site, which encodes a start ATG, followed by 16 nucleotides of the human HESF III coding sequence set out in FIG. 3 (SEQ ID NO:5).

The 3' primer has the sequence
for hESF I 5'CGCAAGCTTCATTTTTACATGTCA 3' (SEQ ID NO:10) containing the underlined Hind III restriction site followed by 15 nucleotides complementary to 15 nucleotides of the hESF I non-coding sequence set out in FIG. 1 (SEQ ID NO:1), including the stop codon.

for hESF II 5'CGCAAGCTTAGTTTTTACATGTCA 3' (SEQ ID NO:11) containing the underlined Hind III restriction site followed by 15 nucleotides complementary to the last 15 nucleotides of the hESF II non-coding sequence set out in FIG. 2 (SEQ ID NO:3), including the stop codon.

for hESF III 5'CGC AAG CTT ACG CCT TGG GTA AAG TTA 3' (SEQ ID NO:12) containing the underlined HindIII restriction site followed by 18 nucleotides complementary to hESF III non-coding sequence set out in FIG. 3 (SEQ ID NO:5), including the stop codon.

The restrictions sites were convenient to restriction enzyme sites in the bacterial expression vectors pQE-60 (hESF I and II), (Qiagen, Inc.) which were used for bacterial expression in these examples. (Qiagen, Inc. Chatsworth, Calif.). pQE-60 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified human hESF I, II and III DNA and the vector pQE-60 both were digested with Sph I and Hind III (hESF I), Nco I and HindIII (hESF II) and SphI and HindIII (hESF III) and the digested DNAs then were ligated together. Insertion of the hESF I DNA into the restricted vector placed the respective coding regions downstream of and operably linked to the vector's IPTG-inducible promoter and in-frame with an initiating AUG appropriately positioned for translation of hESF I, II and III.

The ligation mixture was transformed into competent E. coli cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). E. coli strain M15/rep4, containing multiple copies of the plasmid pREP4, which expresses lac repressor and confers kanamycin resistance ("Kanr"), was used in carrying out the illustrative example described here. This strain, which is only one of many that are suitable for expressing hESF I, II and III is available commercially from Qiagen.

Transformants were identified by their ability to grow on LB plates in the presence of ampicillin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 µg/ml) and kanamycin (25 µg/ml).

The O/N culture was used to inoculate a large culture, at a dilution of approximately 1:100 to 1:250. The cells were grown to an optical density at 600nm ("OD600") of between 0.4 and 0.6. Isopropyl-B-D-thiogalactopyranoside ("IPTG") was then added to a final concentration of 1 mM to induce transcription from lac repressor sensitive promoters, by inactivating the laci repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea solution containing the solubilized protein was passed over a PD-10 column in 2× phosphate buffered saline ("PBS"), thereby removing the urea, exchanging the buffer and refolding the protein. The protein was purified by a further step of chromatography to remove endotoxin. Then, it was sterile filtered. The sterile filtered protein preparation was stored in 2× PBS at a concentration of 95 micrograms per mL.

Analysis of the preparation by standard methods of polyacrylamide gel electrophoresis revealed that the preparation contained about 95% monomer hESF I, II and III having the expected molecular weight.

Example 2

Cloning and expression of human hESF I, II and III in a baculovirus expression system The cDNA sequence encoding the full length human hESF I, II and III protein, in the deposited clone is amplified using PCR oligonucleotide primers corresponding to the 5' and 3' sequences of the gene:

for hESF I the 5' primer has the sequence 5'CCCGGATCC GCCATCATGAGGCTGTCAGTGTGTCT 3' (SEQ ID NO:13) containing the BamHI restriction enzyme site (bold) followed by a kozak sequence (GCC ATC) and 20 bases of the sequence of hESF I of FIG. 1 (SEQ ID NO:1);

for hESF II the 5' primer has the sequence 5'CGC GGA TCC GCC ATC ATG AAG CTG TCG GTG 3' (SEQ ID NO:14) containing the BamHI restriction enzyme site (bold) followed by 15 bases of the sequence of hESF II of FIG. 2 (SEQ ID NO:3);

for hESF III the 5' primer has the sequence 5'CGC GGA TCC GCC ATC ATG AAG CTG CTG ATG GTC 3' (SEQ ID NO:15) containing the BamHI restriction enzyme site (bold) followed by 15 bases of the sequence of hESF III of FIG. 3 (SEQ ID NO:5).

Inserted into an expression vector, as described below, the 5' end of the amplified fragment encoding human hESF I, II or III provides an efficient signal peptide. An efficient signal for initiation of translation in eukaryotic cells, as described by Kozak, M., J. Mol. Biol. 196: 947–950 (1987) is appropriately located in the vector portion of the construct.

For HESF I the 3' primer has the sequence 5'CCCGG-TACC TTTTTTTTTTTTTTTTTT 3' (SEQ ID NO:16) containing the underlined Asp718 restriction site followed by 18 nucleotides complementary to the poly A tail;

for hESF II the 3' primer has the sequence 5'CGC GGTACCACGCCTTGGGTAAAGTTA 3' (SEQ ID NO:17) containing the underlined Asp718 restriction followed by nucleotides complementary to 15 nucleotides of the hESF II non-coding sequence set out in FIG. 2 (SEQ ID NO:3), including the stop codon;

for hESF III the 3' primer has the sequence 5'CGC GGT ACC ACG CCT TGG GTA AAG TTA 3' (SEQ ID NO:18) containing the underlined Asp718 restriction followed by nucleotides complementary to 18 nucleotides of the hESF III non-coding sequence set out in FIG. 3 (SEQ ID NO:5), including the stop codon.

The amplified fragments are isolated from a 1% agarose gel using a commercially available kit ("Geneclean," BIO 101 Inc., La Jolla, Calif.). The fragments then are digested with the respective restriction enzymes and again are purified on a 1% agarose gel. This fragments are designated herein F2.

The vector pRG1 is used to express the hESF I, II or III protein in the baculovirus expression system, using standard methods, such as those described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the Autographa californica nuclear polyhedrosis virus (AcMNPV) followed by convenient restriction sites. The polyadenylation site of the simian virus 40 ("SV40") is used for efficient polyadenylation. For an easy selection of recombinant virus the beta-galactosidase gene from E.coli is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIMI provided, as those of skill readily will appreciate, that construction provides appropriately located signals for transcription, translation, trafficking and the like. Such vectors are described in Luckow et al., Virology 170: 31-39, among others.

The plasmid is digested with the respective restriction enzymes and then is dephosphorylated using calf intestinal phosphatase, using routine procedures known in the art. The DNA is then isolated from a 1% agarose gel using a commercially available kit ("Geneclean" BIO 101 Inc., La Jolla, Ca.). This vector DNA is designated herein "V2".

Fragments F2 and the dephosphorylated plasmid V2 are ligated together with T4 DNA ligase. *E.coli* HB101 cells are transformed with ligation mix and spread on culture plates. Bacteria are identified that contain the plasmid with the human hESF I, II or III gene by digesting DNA from individual colonies using the respective restriction enzymes and then analyzing the digestion product by gel electrophoresis. The sequence of the cloned fragment is confirmed by DNA sequencing. This plasmid is designated herein pBachESF I, II or III.

5 μg of the plasmid pBachESF I, II or III is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84: 7413–7417 (1987). lyg of BaculoGold™ virus DNA and 5 μg of the plasmid pBachESF I, II or III are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted hESF I, II or III is identified by DNA analysis including restriction mapping and sequencing. This is designated herein as V-hESF I, II or III.

Sf9 cells are grown in Grace's medium supplemented with 10% heat-inactivated FBS. The cells are infected with the recombinant baculovirus V-hESF I, II or III at a multiplicity of infection ("MOI") of about 2. Six hours later the medium is removed and is replaced with SF900 II medium minus methionine and cysteine (available from Life Technologies Inc., Gaithersburg). 42 hours later, 5 µCi of 35S-methionine and 5 µCi 35S cysteine (available from Amersham) are added. The cells are further incubated for 16 hours and then they are harvested by centrifugation, lysed and the labeled proteins are visualized by SDS-PAGE and autoradiography.

Example 3
Expression of hESF I, II and III in COS Cells

The expression plasmid, hESF I, II and III HA, is made by cloning a cDNA encoding hESF I, II and III into the expression vector pcDNAI/Amp (which can be obtained from Invitrogen, Inc.).

The expression vector pcDNAI/amp contains: (1) an E.coli origin of replication effective for propagation in E. coli and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire hESF I, II and III precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984) The fusion of the HA tag to the target protein allows easy detection of the recombinant protein with an antibody that recognizes the HA epitope.

The plasmid construction strategy is as follows:

The hESF I, II and III cDNA of the deposit clone is amplified using primers that contained convenient restriction sites, much as described above regarding the construction of expression vectors for expression of hESF I, II and III in E. coli and S. fugiperda.

To facilitate detection, purification and characterization of the expressed HESF I, II and III, one of the primers contains a heamaglutinin tag ("HA tag") as described above.

Suitable primers include that following, which are used in this example:

The 5' primer, containing the underlined BamHI site, an AUG start codon and has the following sequence. 5'CGC GGA TCC ACC ATG GTC TCG CTG GCC CTT 3' (SEQ ID NO:19) (ESFI); 5'CGC GGA TCC ACC ATG AAG CTG TCG GTG TGT 3' (SEQ ID NO:20) (ESFII); 5'CGC GGA TCC ACC ATG AAG CTG CTG ATG GTC 3' (SEQ ID NO:21) (ESFIII).

The 3' primer, containing the underlined XbaI site, stop codon, HA tag and 15 bp of 3' coding sequence (at the 3' end) has the following sequence: 5'CGC TCT AGA TCA AGC GTA GTC TGG GAC GTC GTA TGG GTA CAC ACC ACA TTT TTT 3' (SEQ ID NO:22) (ESFI); 5'CGC TCT AGA TCA AGC GTA GTC TGG GAC GTC GTA TGG GTA CAC ACT ACA TTT CTT 3' (SEQ ID NO:23) (ESFII); 5'CGC TCT AGA TCA AGC GTA GTC TGG GAC GTC GTA TGG GTA ATT ACT CTT CAT ATT 3' (SEQ ID NO:24) (ESFIII).

The PCR amplified DNA fragment and the vector, pcDNAI/Amp, are digested with and then ligated. The ligation mixture is transformed into E. coli strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the hESF I, II and III-encoding fragment.

For expression of recombinant hESF I, II and III, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989). Cel l s a re incubated under conditicns for expression of hESF I, II and III by the vector.

Expression of the hESF I, II and III HA fusion protein is detected by radiolabelling and immunoprecipitation, using methods described in, for example Harlow et al., ANTI-BODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4
Tissue Distribution of hESF I, II and III Expression

Northern blot analysis is carried out to examine the levels of expression of hESF I, II and III in human tissues, using methods described by, among others, Sambrook et al, cited above. Total cellular RNA samples are isolated with RNA-zol™ B system (Biotecx Laboratories, Inc. 6023 South Loop East, Houston, TX 77033).

About 10 µg of Total RNA is isolated from tissue samples. The RNA is size resolved by electrophoresis through a 1% agarose gel under strongly denaturing conditions. RNA is blotted from the gel onto a nylon filter, and the filter then is prepared for hybridization to a detectably labeled polynucleotide probe.

As a probe to detect mRNA that encodes hESF I, II and III, the antisense strand of the coding region of the cDNA insert in the deposited clone is labeled to a high specific activity. The cDNA is labeled by primer extension, using the Prime-It kit, available from Stratagene. The reaction is carried out using 50 μg of the cDNA, following the standard reaction protocol as recommended by the supplier. The labeled polynucleotide is purified away from other labeled reaction components by column chromatography using a Select-G-50 column, obtained from 5-Prime - 3-Prime, Inc. of 5603 Arapahoe Road, Boulder, Colo. 80303.

The labeled probe is hybridized to the filter, at a concentration of 1,000,000 cpm/ml, in a small volume of 7% SDS, 0.5 M NaPO4, pH 7.4 at 65° C., overnight.

Thereafter the probe solution is drained and the filter is washed twice at room temperature and twice at 60° C. with 0.5×SSC, 0.1% SDS. The filter then is dried and exposed to film at −70° C. overnight with an intensifying screen.

Example 5
Gene Therapeutic Expression of Human hESF I, II and III

Fibroblasts are obtained from a subject by skin biopsy. The resulting tissue is placed in tissue-culture medium and separated into small pieces. Small chunks of the tissue are placed on a wet surface of a tissue culture plask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

hESF I, II and III cDNA capable of expressing active hESF I, II and III, is isolated. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the HESF I, II or III fragment are mixed together and joined using T4 DNA ligase. The ligation mixture is used to transform *E. Coli* and the bacteria are then plated onto agarcontaining kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the hESF I, II or III gene is introduced into the packaging cells by standard techniques. Infectious viral particles containing the hESF I, II or III gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce hESF I, II or III product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. An isolated polypeptide comprising an amino acid sequence selected from the group consisting of:
   (a) amino acids 1–69 of SEQ ID NO:2;
   (b) amino acids -21–69 of SEQ ID NO:2;
   (c) a polypeptide encoded by the cDNA contained in ATCC Deposit No. 97401;
   (d) a mature polypeptide encoded by the cDNA contained in ATCC Deposit No. 97401;
   (e) at least 30 contiguous amino acids of SEQ ID NO:2;
   (f) at least 50 contiguous amino acids of SEQ ID NO:2;
   (g) amino acids 1–69 of SEQ ID NO:4;
   (h) amino acids -21–69 of SEQ ID NO:4;
   (i) a polypeptide encoded by the cDNA contained in ATCC Deposit No. 97402;
   (j) a mature polypeptide encoded by the cDNA contained in ATCC Deposit No. 97402;
   (k) at least 30 contiguous amino acids of SEQ ID NO:4;
   (l) at least 50 contiguous amino acids of SEQ ID NO:4;
   (m) amino acids 1–74 of SEQ ID NO:6;
   (n) amino acids -21–74 of SEQ ID NO:6;
   (o) a polypeptide encoded by the cDNA contained in ATCC Deposit No. 97403;
   (p) a mature polypeptide encoded by the cDNA contained in ATCC Deposit No. 97403;
   (q) at least 30 contiguous amino acids of SEQ ID NO:6; and
   (r) at least 50 contiguous amino acids of SEQ ID NO:6.

2. The isolated polypeptide of claim 1, wherein said amino acid sequence is (a).
3. The isolated polypeptide of claim 1, wherein said amino acid sequence is (b).
4. The isolated polypeptide of claim 1, wherein said amino acid sequence is (c).
5. The isolated polypeptide of claim 1, wherein said amino acid sequence is (d).
6. The isolated polypeptide of claim 1, wherein said amino acid sequence is (e).
7. The isolated polypeptide of claim 1, wherein said amino acid sequence is (f).
8. The isolated polypeptide of claim 1, wherein said amino acid sequence is (g).
9. The isolated polypeptide of claim 1, wherein said amino acid sequence is (h).
10. The isolated polypeptide of claim 1, wherein said amino acid sequence is (i).
11. The isolated polypeptide of claim 1, wherein said amino acid sequence is (j).
12. The isolated polypeptide of claim 1, wherein said amino acid sequence is (k).
13. The isolated polypeptide of claim 1, wherein said amino acid sequence is (l).
14. The isolated polypeptide of claim 1, wherein said amino acid sequence is (m).
15. The isolated polypeptide of claim 1, wherein said amino acid sequence is (n).
16. The isolated polypeptide of claim 1, wherein said amino acid sequence is (o).
17. The isolated polypeptide of claim 1, wherein said amino acid sequence is (p).
18. The isolated polypeptide of claim 1, wherein said amino acid sequence is (q).
19. The isolated polypeptide of claim 1, wherein said amino acid sequence is (r).
20. The isolated polypeptide of claim 1 further comprising a heterologous polypeptide.
21. An isolated polypeptide produced by the method comprising:
   (a) expressing the polypeptide of claim 1 from a host cell; and
   (b) recovering said polypeptide.
22. An isolated polypeptide comprising a first amino acid sequence at least 90% identical to a second amino acid sequence selected from the group consisting of:
   a) a polypeptide fragment of SEQ ID NO:2 or a polypeptide fragment encoded by the cDNA contained in ATCC Deposit No. 97401, wherein the polypeptide fragment binds an antibody having specificity for the polypeptide of SEQ ID NO:2;

b) a polypeptide fragment of SEQ ID NO:2 or a polypeptide fragment encoded by the cDNA contained in ATCC Deposit No. 97401, wherein said fragment controls growth of endometrial cells;

c) a polypeptide fragment of SEQ ID NO:4 or a polypeptide fragment encoded by the cDNA contained in ATCC Deposit No. 97402, wherein the polypeptide fragment binds an antibody having specificity for the polypeptide of SEQ ID NO:4;

d) a polypeptide fragment of SEQ ID NO:4 or a polypeptide fragment encoded by the cDNA contained in ATCC Deposit No. 97402, wherein said fragment controls growth of endometrial cells;

e) a polypeptide fragment of SEQ ID NO:6 or a polypeptide fragment encoded by the cDNA contained in ATCC Deposit No. 97403, wherein the polypeptide fragment binds an antibody having specificity for the polypeptide of SEQ ID NO:6; and f) a polypeptide fragment of SEQ ID NO:6 or a polypeptide fragment encoded by the cDNA contained in ATCC Deposit No. 97403, wherein said fragment controls growth of endometrial cells.

23. The isolated polypeptide of claim 22, wherein said first amino acid sequence is at least 90% identical to (a).

24. The isolated polypeptide of claim 23, wherein said first amino acid sequence is at least 95% identical to (a).

25. The isolated polypeptide of claim 24, wherein said first amino acid sequence is (a).

26. The isolated polypeptide of claim 22, wherein said first amino acid sequence is at least 90% identical to (b).

27. The isolated polypeptide of claim 26, wherein said first amino acid sequence is at least 95% identical to (b).

28. The isolated polypeptide of claim 27, wherein said first amino acid sequence is (b).

29. The isolated polypeptide of claim 22, wherein said first amino acid sequence is at least 90% identical to (c).

30. The isolated polypeptide of claim 29, wherein said first amino acid sequence is at least 95% identical to (c).

31. The isolated polypeptide of claim 30, wherein said first amino acid sequence is (c).

32. The isolated polypeptide of claim 22, wherein said first amino acid sequence is at least 90% identical to (d).

33. The isolated polypeptide of claim 32, wherein said first amino acid sequence is at least 95% identical to (d).

34. The isolated polypeptide of claim 33, wherein said first amino acid sequence is (d).

35. The isolated polypeptide of claim 22, wherein said first amino acid sequence is at least 90% identical to (e).

36. The isolated polypeptide of claim 35, wherein said first amino acid sequence is at least 95% identical to (e).

37. The isolated polypeptide of claim 36, wherein said first amino acid sequence is (e).

38. The isolated polypeptide of claim 22, wherein said first amino acid sequence is at least 90% identical to (f).

39. The isolated polypeptide of claim 38, wherein said first amino acid sequence is at least 95% identical to (f).

40. The isolated polypeptide of claim 39, wherein said first amino acid sequence is (f).

41. The isolated polypeptide of claim 22 further comprising a heterologous polypeptide.

42. An isolated polypeptide produced by the method comprising:
(a) expressing the polypeptide of claim 22 from a host cell; and
(b) recovering said polypeptide.

43. An isolated polypeptide comprising an amino acid sequence selected from the group consisting of:

(a) amino acid residue 1 to amino acid residue 69 as set forth in SEQ ID NO:2, in which 1 to 5 amino acid residues are substituted, deleted or added, in any combination and in which the polypeptide retains biological activity;

(b) amino acid residue 1 to amino acid residue 69 as set forth in SEQ ID NO:2, in which 5 to 10 amino acid residues are substituted, deleted or added, in any combination and in which the polypeptide retains biological activity;

(c) amino acid residue -21 to amino acid residue 69 as set forth in SEQ ID NO:2, in which 1 to 5 amino acid residues are substituted, deleted or added, in any combination and in which the polypeptide retains biological activity;

(d) amino acid residue -21 to amino acid residue 69 as set forth in SEQ ID NO:2, in which 5 to 10 amino acid residues are substituted, deleted or added, in any combination and in which the polypeptide retains biological activity;

(e) amino acid residue 1 to amino acid residue 69 as set forth in SEQ ID NO:4, in which 1 to 5 amino acid residues are substituted, deleted or added, in any combination and in which the polypeptide retains biological activity;

(f) amino acid residue 1 to amino acid residue 69 as set forth in SEQ ID NO:4, in which 5 to 10 amino acid residues are substituted, deleted or added, in any combination and in which the polypeptide retains biological activity;

(g) amino acid residue -21 to amino acid residue 69 as set forth in SEQ ID NO:4, in which 1 to 5 amino acid residues are substituted, deleted or added, in any combination and in which the polypeptide retains biological activity;

(h) amino acid residue -21 to amino acid residue 69 as set forth in SEQ ID NO:4, in which 5 to 10 amino acid residues are substituted, deleted or added, in any combination and in which the polypeptide retains biological activity;

(i) amino acid residue 1 to amino acid residue 74 as set forth in SEQ ID NO:6, in which 1 to 5 amino acid residues are substituted, deleted or added, in any combination and in which the polypeptide retains biological activity;

(j) amino acid residue 1 to amino acid residue 74 as set forth in SEQ ID NO:6, in which 5 to 10 amino acid residues are substituted, deleted or added, in any combination and in which the polypeptide retains biological activity;

(k) amino acid residue -21 to amino acid residue 74 as set forth in SEQ ID NO:6, in which 1 to 5 amino acid residues are substituted, deleted or added, in any combination and in which the polypeptide retains biological activity; and (l) amino acid residue -21 to amino acid residue 74 as set forth in SEQ ID NO:6, in which 5 to 10 amino acid residues are substituted, deleted or added, in any combination and in which the polypeptide retains biological activity.

44. The isolated polypeptide of claim 43, wherein said amino acid sequence is (a).

45. The isolated polypeptide of claim 43, wherein said amino acid sequence is (b).

46. The isolated polypeptide of claim 43, wherein said amino acid sequence is (c).

47. The isolated polypeptide of claim 43, wherein said amino acid sequence is (d).

48. The isolated polypeptide of claim 43, wherein said amino acid sequence is (e).

49. The isolated polypeptide of claim 43, wherein said amino acid sequence is (f).

50. The isolated polypeptide of claim 43, wherein said amino acid sequence is (g).

51. The isolated polypeptide of claim 43, wherein said amino acid sequence is (h).

52. The isolated polypeptide of claim 43, wherein said amino acid sequence is (i).

53. The isolated polypeptide of claim 43, wherein said amino acid sequence is (j).

54. The isolated polypeptide of claim 43, wherein said amino acid sequence is (k).

55. The isolated polypeptide of claim 43, wherein said amino acid sequence is (l).

56. The isolated polypeptide of claim 43 further comprising a heterologous polypeptide; wherein said first amino acid sequence has human endometrial steroid-binding factor I, II or III activity.

57. An isolated polypeptide produced by the method comprising:
    (a) expressing the polypeptide of claim 43 from a host cell; and
    (b) recovering said polypeptide.

58. An isolated polypeptide comprising a first amino acid sequence at least 90% identical to a second amino acid sequence selected from the group consisting of:
    (a) amino acids 1–69 of SEQ ID NO:2;
    (b) amino acids -21–69 of SEQ ID NO:2;
    (c) a polypeptide encoded by the cDNA contained in ATCC Deposit No. 97401;
    (d) a mature polypeptide encoded by the cDNA contained in ATCC Deposit No. 97401;
    (e) at least 30 contiguous amino acids of SEQ ID NO:2;
    (f) at least 50 contiguous amino acids of SEQ ID NO:2;
    (g) amino acids 1–69 of SEQ ID NO:4;
    (h) amino acids -21–69 of SEQ ID NO:4;
    (i) a polypeptide encoded by the cDNA contained in ATCC Deposit No. 97402;
    (j) a mature polypeptide encoded by the cDNA contained in ATCC Deposit No. 97402;
    (k) at least 30 contiguous amino acids of SEQ ID NO:4;
    (l) at least 50 contiguous amino acids of SEQ ID NO:4;
    (m) amino acids 1–74 of SEQ ID NO:6;
    (n) amino acids -21–74 of SEQ ID NO:6;
    (o) a polypeptide encoded by the cDNA contained in ATCC Deposit No. 97403;
    (p) a mature polypeptide encoded by the cDNA contained in ATCC Deposit No. 97403;
    (q) at least 30 contiguous amino acids of SEQ ID NO:6; and
    (r) at least 50 contiguous amino acids of SEQ ID NO:6.

59. The isolated polypeptide of claim 58, wherein said first amino acid sequence is at least 90% identical to (a).

60. The isolated polypeptide of claim 59, wherein said first amino acid sequence is at least 95% identical to (a).

61. The isolated polypeptide of claim 58, wherein said first amino acid sequence is at least 90% identical to (b).

62. The isolated polypeptide of claim 61, wherein said first amino acid sequence is at least 95% identical to (b).

63. The isolated polypeptide of claim 58, wherein said first amino acid sequence is at least 90% identical to (c).

64. The isolated polypeptide of claim 63, wherein said first amino acid sequence is at least 95% identical to (c).

65. The isolated polypeptide of claim 58, wherein said first amino acid sequence is at least 90% identical to (d).

66. The isolated polypeptide of claim 65, wherein said first amino acid sequence is at least 95% identical to (d).

67. The isolated polypeptide of claim 58, wherein said first amino acid sequence is at least 90% identical to (e).

68. The isolated polypeptide of claim 67, wherein said first amino acid sequence is at least 95% identical to (e).

69. The isolated polypeptide of claim 58, wherein said first amino acid sequence is at least 90% identical to (f).

70. The isolated polypeptide of claim 69, wherein said first amino acid sequence is at least 95% identical to (f).

71. The isolated polypeptide of claim 58, wherein said first amino acid sequence is at least 90% identical to (g).

72. The isolated polypeptide of claim 71, wherein said first amino acid sequence is at least 95% identical to (g).

73. The isolated polypeptide of claim 58, wherein said first amino acid sequence is at least 90% identical to (h).

74. The isolated polypeptide of claim 73, wherein said first amino acid sequence is at least 95% identical to (h).

75. The isolated polypeptide of claim 58, wherein said first amino acid sequence is at least 90% identical to (i).

76. The isolated polypeptide of claim 75, wherein said first amino acid sequence is at least 95% identical to (i).

77. The isolated polypeptide of claim 58, wherein said first amino acid sequence is at least 90% identical to (j).

78. The isolated polypeptide of claim 77, wherein said first amino acid sequence is at least 95% identical to (j).

79. The isolated polypeptide of claim 58, wherein said first amino acid sequence is at least 90% identical to (k).

80. The isolated polypeptide of claim 79, wherein said first amino acid sequence is at least 95% identical to (k).

81. The isolated polypeptide of claim 58, wherein said first amino acid sequence is at least 90% identical to (l).

82. The isolated polypeptide of claim 81, wherene said first amino acid sequence is at least 95% acid identical to (l).

83. The isolated polypeptide of claim 58, wherein said first amino acid sequence is at least 90% identical to (m).

84. The isolated polypeptide of claim 83, wherein said first amino acid sequence is at least 95% identical to (m).

85. The isolated polypeptide of claim 58, wherein said first amino acid sequence is at least 90% identical to (n).

86. The isolated polypeptide of claim 85, wherein said first amino acid sequence is at least 95% identical to (n).

87. The isolated polypeptide of claim 58, wherein said first amino acid sequence is at least 90% identical to (o).

88. The isolated polypeptide of claim 87, wherein said first amino acid sequence is at least 95% identical to (o).

89. The isolated polypeptide of claim 58, wherein said first amino acid sequence is at least 90% identical to (p).

90. The isolated polypeptide of claim 89, wherein said first amino acid sequence is at least 95% identical to (p).

91. The isolated polypeptide of claim 58, wherein said first amino acid sequence is at least 90% identical to (q).

92. The isolated polypeptide of claim 91, wherein said first amino acid sequence is at least 95% identical to (q).

93. The isolated polypeptide of claim 58, wherein said first amino acid sequence is at least 90% identical to (r).

94. The isolated polypeptide of claim 93, wherein said first amino acid sequence is at least 95% identical to (r).

95. The isolated polypeptide of claim 58 further comprising a heterologous polypeptide.

96. An isolated polypeptide produced by the method comprising:
    (a) expressing the polypeptide of claim 58 from a host cell; and
    (b) recovering said polypeptide.

* * * * *

UNITED STATES PATENT AND TRADEMARK OFFICE
CERTIFICATE OF CORRECTION

PATENT NO.    : 6,174,992 B1  Page 1 of 1
DATED         : January 16, 2001
INVENTOR(S)   : Jian Ni, Guo-Liang Yu and Reiner Gentz It is certified that error appears in the above-identified patent and that said Letters Patent is hereby corrected as shown below:

Column 58,
Line 33, please delete "wherene" and replace it with -- wherein --.

Signed and Sealed this

Thirtieth Day of July, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 433 BASE PAIRS
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO:1:

```
TCACTCATTG TGAAAGCTGA GCTCACAGCC GAATAAGCCA CC ATG AGG CTG TCA      54
                                              Met Arg Leu Ser
                                              -21 -20
```

```
GTG TGT CTC CTG ATG GTC TCG CTG GCC CTT TGC TGC TAC CAG GCC CAT      102
Val Cys Leu Leu Met Val Ser Leu Ala Leu Cys Cys Tyr Gln Ala His
        -15                 -10                 -5

GCT CTT GTC TGC CCA GCT GTT GCT TCT GAG ATC ACA GTC TTC TTA TTC      150
Ala Leu Val Cys Pro Ala Val Ala Ser Glu Ile Thr Val Phe Leu Phe
 1              5                   10                  15

TTA AGT GAC GCT GCG GTA AAC CTC CAA GTT GCC AAA CTT AAT CCA CCT      198
Leu Ser Asp Ala Ala Val Asn Leu Gln Val Ala Lys Leu Asn Pro Pro
            20                  25                  30

CCA GAA GCT CTT GCA GCC AAG TTG GAA GTG AAG CAC TGC ACC GAT CAG      246
Pro Glu Ala Leu Ala Ala Lys Leu Glu Val Lys His Cys Thr Asp Gln
                35                  40                  45

ATA TCT TTT AAG AAA CGA CTC TCA TTG GAA AAA GTC CTG GTG GAA ATA      294
Ile Ser Phe Lys Lys Arg Leu Ser Leu Glu Lys Val Leu Val Glu Ile
        50                  55                  60

GTG AAA AAA TGT GGT GTG TGACATGTAA AAATGCTCAA CCTGGTTTCC             342
Val Lys Lys Cys Gly Val
        65

AAAGTCTTTC AACGACACCC TGATCTTCAC TAAAAATTGT AAAGGTTTCA ACACGTTGCT    402

TTAATAAATC ACTTGCCCTG CACATCAAAA A                                   433

(2) INFORMATION FOR SEQ ID NO:2:

(i) SEQUENCE CHARACTERISTICS:
        (A) LENGTH: 90 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

Met Arg Leu Ser Val Cys Leu Leu Met Val Ser Leu Ala Leu Cys
-21 -20             -15                 -10

Cys Tyr Gln Ala His Ala Leu Val Cys Pro Ala Val Ala Ser Glu
        -5              1               5

Ile Thr Val Phe Leu Phe Leu Ser Asp Ala Ala Val Asn Leu Gln
10                  15                  20

Val Ala Lys Leu Asn Pro Pro Glu Ala Leu Ala Ala Lys Leu
                25                  30                  35

Glu Val Lys His Cys Thr Asp Gln Ile Ser Phe Lys Lys Arg Leu
            40                  45                  50

Ser Leu Glu Lys Val Leu Val Glu Ile Val Lys Lys Cys Gly Val
            55                  60                  65

(2) INFORMATION FOR SEQ ID NO:3:

(i) SEQUENCE CHARACTERISTICS:
        (A) LENGTH: 436 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:3:

TTGTTTGTGA AAGCTGAGCT CACAGCAAAA CAAGCCACC ATG AAG CTG TCG GTG       54
                                           Met Lys Leu Ser Val
                                           -21 -20

TGT CTC CTG CTG GTC ACG CTG GCC CTC TGC TGC TAC CAG GCC AAT GCC     102
Cys Leu Leu Leu Val Thr Leu Ala Leu Cys Cys Tyr Gln Ala Asn Ala
        -15                 -10                 -5
```

-continued

```
GAG TTC TGC CCA GCT CTT GTT TCT GAG CTG TTA GAC TTC TTC TTC ATT        150
Glu Phe Cys Pro Ala Leu Val Ser Glu Leu Leu Asp Phe Phe Phe Ile
 1            5                  10                  15

AGT GAA CCT CTG TTC AAG TTA AGT CTT GCC AAA TTT GAT GCC CCT CCG        198
Ser Glu Pro Leu Phe Lys Leu Ser Leu Ala Lys Phe Asp Ala Pro Pro
                20                  25                  30

GAA GCT GTT GCA GCC AAG TTA GGA GTG AAG AGA TGC ACG GAT CAG ATG        246
Glu Ala Val Ala Ala Lys Leu Gly Val Lys Arg Cys Thr Asp Gln Met
            35                  50                  45

TCC CTT CAG AAA CGA AGC CTC ATT GCG GAA GTC CTG GTG AAA ATA TTG        294
Ser Leu Gln Lys Arg Ser Leu Ile Ala Glu Val Leu Val Lys Ile Leu
50                      55                  60

AAG AAA TGT AGT GTG TGACATGTAA AAACTTTCAT CCTGGTTTCC ACTGTCTTTC        349
Lys Lys Cys Ser Val
65

AATGACACCC TGATCTTCAC TGCAGAATGT AAAGGTTTCA ACGTCTTGCT TTAATAAATC      409

ACTTGCTCTC CAAAAAAAAA AAAAAAA                                          436
```

(2) INFORMATION FOR SEQ ID NO:4:

(i) SEQUENCE CHARACTERISTICS:
        (A) LENGTH: 90 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:4:

```
Met Lys Leu Ser Val Cys Leu Leu Val Thr Leu Ala Leu Cys
-21 -20                 -15                 -10

Cys Tyr Gln Ala Asn Ala Glu Phe Cys Pro Ala Leu Val Ser Glu
     -5                   1                  5

Leu Leu Asp Phe Phe Phe Ile Ser Glu Pro Leu Phe Lys Leu Ser
10                  15                  20

Leu Ala Lys Phe Asp Ala Pro Pro Glu Ala Val Ala Ala Lys Leu
             25                  30                  35

Gly Val Lys Arg Cys Thr Asp Gln Met Ser Leu Gln Lys Arg Ser
         40                  45                  50

Leu Ile Ala Glu Val Leu Val Lys Ile Leu Lys Lys Cys Ser Val
         55                  60                  65
```

(2) INFORMATION FOR SEQ ID NO:5:

(i) SEQUENCE CHARACTERISTICS:
        (A) LENGTH: 476 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:5:

```
ACGAGCTGCC ACGCACGACT GAACACAGAC AGCAGCCGCC TCGCC ATG AAG CTG          54
                                                 Met Lys Leu
                                                 -21 -20

CTG ATG GTC CTC ATG CTG GCG GCC CTC CTC CTG CAC TGC TAT GCA GAT       102
Leu Met Val Leu Met Leu Ala Ala Leu Leu Leu His Cys Tyr Ala Asp
        -15                 -10                  -5

TCT GGC TGC AAA CTC CTG GAG GAC ATG GTT GAA AAG ACC ATC AAT TCC       150
Ser Gly Cys Lys Leu Leu Glu Asp Met Val Glu Lys Thr Ile Asn Ser
 1               5                  10
```

```
GAC ATA TCT ATA CCT GAA TAC AAA GAG CTT CTT CAA GAG TTC ATA GAC      198
Asp Ile Ser Ile Pro Glu Tyr Lys Glu Leu Leu Gln Glu Phe Ile Asp
 15              20                  25                  30

AGT GAT GCC GCT GCA GAG GCT ATG GGG AAA TTC AAG CAG TGT TTC CTC      246
Ser Asp Ala Ala Ala Glu Ala Met Gly Lys Phe Lys Gln Cys Phe Leu
             35                  40                  45

AAC CAG TCA CAT AGA ACT CTG AAA AAC TTT GGA CTG ATG ATG CAT ACA      294
Asn Gln Ser His Arg Thr Leu Lys Asn Phe Gly Leu Met Met His Thr
         50                  55                  60

GTG TAC GAC AGC ATT TGG TGT AAT ATG AAG AGT AAT TAACTTTACC           340
Val Tyr Asp Ser Ile Trp Cys Asn Met Lys Ser Asn
     65                  70

CAAGGCGTTT GGCTCAGAGG GCTACAGACT ATGGCCAGAA CTCATCTGTT GATTGCTAGA    400

AACCACTTTC TTCTTGTGTT GCTTTTTATG TGGGAACTGC TAGACAACTG TTGAAACCTC    460

AATTCATTCC ATTTCA                                                    476

(2) INFORMATION FOR SEQ ID NO:6:

(i) SEQUENCE CHARACTERISTICS:
        (A) LENGTH: 95 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:6:

Met Lys Leu Leu Met Val Leu Met Leu Ala Ala Leu Leu Leu His
-21 -20             -15             -10

Cys Tyr Ala Asp Ser Gly Cys Lys Leu Leu Glu Asp Met Val Glu
 -5              1               5

Lys Thr Ile Asn Ser Asp Ile Ser Ile Pro Glu Tyr Lys Glu Leu
 10              15              20

Leu Gln Glu Phe Ile Asp Ser Asp Ala Ala Ala Glu Ala Met Gly
 25              30              35

Lys Phe Lys Gln cys Phe Leu Asn Gln Ser His Arg Thr Leu Lys
 40              45              50

Asn Phe Gly Leu Met Met His Thr Val Tyr Asp Ser Ile Trp Cys
 55              60              65

Asn Met Lys Ser Asn
 70

(2) INFORMATION FOR SEQ ID NO:7:

(i) SEQUENCE CHARACTERISTICS:
        (A) LENGTH: 24 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:7:

CGCGCATGCT TGTCTGCCCA GCTG                                            24

(2) INFORMATION FOR SEQ ID NO:8:

(i) SEQUENCE CHARACTERISTICS:
        (A) LENGTH: 24 BASE PAIRS
        (B) TYPE: NUCLEIC ACID
        (C) STRANDEDNESS: SINGLE
        (D) TOPOLOGY: LINEAR
```

(ii) MOLECULE TYPE: Oligonucleotide (xi) SEQUENCE DESCRIPTION: SEQ ID NO:8:

CGCCCATGGA GTTCTGCCCA GCTC                                    24

(2) INFORMATION FOR SEQ ID NO:9:

(i) SEQUENCE CHARACTERISTICS:
        (A) LENGTH: 24 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:9:

CGCGCATGCA CTGCTATGCA GATT                                    24

(2) INFORMATION FOR SEQ ID NO:10:

(i) SEQUENCE CHARACTERISTICS:
        (A) LENGTH: 24 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:10:

CGCAAGCTTC ATTTTTACAT GTCA                                    24

(2) INFORMATION FOR SEQ ID NO:11:

(i) SEQUENCE CHARACTERISTICS:
        (A) LENGTH: 24 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:11:

CGCAAGCTTC ATTTTTACAT GTCA                                    24

(2) INFORMATION FOR SEQ ID NO:12:

(i) SEQUENCE CHARACTERISTICS:
        (A) LENGTH: 27 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:12:

CGCAAGCTTA CGCCTTGGGT AAAGTTA                                 27

(2) INFORMATION FOR SEQ ID NO:13:

(i) SEQUENCE CHARACTERISTICS:
        (A) LENGTH: 35 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:13:

```
CCCGGATCCG CCATCATGAG GCTGTCAGTG TGTCT                                  35

(2) INFORMATION FOR SEQ ID NO:14:

(i) SEQUENCE CHARACTERISTICS:
        (A) LENGTH:  30 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:14:

CGCGGATCCG CCATCATGAA GCTGTCGGTG                                        30

(2) INFORMATION FOR SEQ ID NO:15:

(i) SEQUENCE CHARACTERISTICS:
        (A) LENGTH:  33 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:15:

CGCGGATCCG CCATCATGAA GCTGCTGATG GTC                                    33

(2) INFORMATION FOR SEQ ID NO:16:

(i) SEQUENCE CHARACTERISTICS:
        (A) LENGTH:  27 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:16:

CCCGGTACCT TTTTTTTTTT TTTTTTT                                           27

(2) INFORMATION FOR SEQ ID NO:17:

(i) SEQUENCE CHARACTERISTICS:
        (A) LENGTH:  27 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:17:

CGCGGTACCA CGCCTTGGGT AAAGTTA                                           27

(2) INFORMATION FOR SEQ ID NO:18:

(i) SEQUENCE CHARACTERISTICS:
        (A) LENGTH:  27 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:18:

CGCGGTAACA CGCCTTGGGT AAAGTTA                                           27
```

(2) INFORMATION FOR SEQ ID NO:19:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:19:

CGCGGATCCA CCATGGTCTC GCTGGCCCTT                            30

(2) INFORMATION FOR SEQ ID NO:20:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:20:

CGCGGATCCA CCATGAAGCT GTCGGTGTGT                            30

(2) INFORMATION FOR SEQ ID NO:21:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:21:

CGCGGATCCA CCATGAAGCT GCTGATGGTC                            30

(2) INFORMATION FOR SEQ ID NO:22:

(i) SEQUENCE CHARACTERISTICS:
        (A) LENGTH: 54 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:22:

CGCTCTAGAT CAAGCGTAGT CTGGGACGTC GTATGGGTAC ACACCACATT TTTT        54

(2) INFORMATION FOR SEQ ID NO:23:

(i) SEQUENCE CHARACTERISTICS:
        (A) LENGTH: 54 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:23:

CGCTCTAGAT CAAGCGTAGT CTGGGACGTC GTATGGGTAC ACACTACATT TCTT        54

(2) INFORMATION FOR SEQ ID NO:24:

(i) SEQUENCE CHARACTERISTICS:
        (A) LENGTH: 54 BASE PAIRS (B) TYPE: NUCLEIC ACID
(C) STRANDEDNESS: SINGLE
(D) TOPOLOGY: LINEAR (ii) MOLECULE TYPE: Oligonucleotide (xi) SEQUENCE DESCRIPTION: SEQ ID NO:24:

CGCTCTAGAT CAAGCGTAGT CTGGGACGTC GTATGGGTAA TTACTCTTCA TATT     54

(2) INFORMATION FOR SEQ ID NO:25:

(i) SEQUENCE CHARACTERISTICS:
      (A) LENGTH: 90 AMINO ACIDS
      (B) TYPE: AMINO ACID
      (C) STRANDEDNESS: SINGLE
      (D) TOPOLOGY: LINEAR (ii) MOLECULE TYPE: PROTEIN (xi) SEQUENCE DESCRIPTION: SEQ ID NO:25:

Ile Glu Leu Ser Leu Cys Leu Leu Ile Met Leu Ala Val Cys Cys
                 5                  10                  15

Tyr Glu Ala Asn Ala Ser Gln Ile Cys glu Leu Val Ala His Glu
                20                  25                  30

Thr Ile Ser Phe Leu Met Lys Ser glu Glu Glu Leu Lys Lys Glu
                35                  40                  45

Leu Glu Met Tyr Asn ala Pro Pro Ala Ala Val Glu Ala Lys Leu
                50                  55                  60

Glu Val Lys Arg Cys Val Asp Gln Met Ser Asn Gly Asp Arg Leu
                65                  70                  75

Val Val Ala Glu Thr Leu Val Tyr Ile Phe Leu Glu Cys Gly Val
                80                  85                  90

(2) INFORMATION FOR SEQ ID NO:26:

(i) SEQUENCE CHARACTERISTICS:
      (A) LENGTH: 90 AMINO ACIDS
      (B) TYPE: AMINO ACID
      (C) STRANDEDNESS: SINGLE
      (D) TOPOLOGY: LINEAR (ii) MOLECULE TYPE: PROTEIN (xi) SEQUENCE DESCRIPTION: SEQ ID NO:26:

Ile Glu Leu Ser Leu Cys Leu Leu Ile Met Leu Ala Val Cys Cys
                 5                  10                  15

Tyr Glu Ala Asn Ala Ser Gln Ile Cys Glu Leu Val Ala His Glu
                20                  25                  30

Thr Ile Ser Phe Leu Met Lys Ser Glu Glu Glu Leu Lys Lys Glu
                35                  40                  45

Leu Glu Met Tyr Asn Ala Pro Pro Ala Ala Val Glu Ala Lys Leu
                50                  55                  60

Glu Val Lys Arg Cys Val Asp Gln Met Ser Asn Gly Asp Arg Leu
                65                  70                  75

Val Val Ala Glu Thr Leu Val Tyr Ile Phe Leu Glu Cys Gly Val
                80                  85                  90

(2) INFORMATION FOR SEQ ID NO:27:

(i) SEQUENCE CHARACTERISTICS:
      (A) LENGTH: 95 AMINO ACIDS
      (B) TYPE: AMINO ACID
      (C) STRANDEDNESS: SINGLE

-continued

```
        (D) TOPOLOGY:  LINEAR (ii) MOLECULE TYPE:  PROTEIN (xi) SEQUENCE DESCRIPTION:  SEQ ID NO:27:

Met Lys Leu Val Phe Leu Phe Leu Leu Val Thr Ile Pro Ile Cys
                  5                  10                  15

Cys Tyr Ala Ser Gly Ser Gly Cys Ser Ile Leu Asp Glu Val Ile
                 20                  25                  30

Arg Gly Thr Ile Asn Ser Thr Val Thr Leu His Asp Tyr Met Lys
                 35                  40                  45

Leu Val Lys Pro Tyr Val Gln Ala His Phe Thr Glu Lys Ala Val
                 50                  55                  60

Lys Gln Phe Lys Gln cys Phe Leu Asp Gln Thr Asp Lys Thr Leu
                 65                  70                  75

Glu Asn Val Gly Val Met Met Glu Ala Ile Phe Asn Ser Glu Ser
                 80                  85                  90

Cys Gln Gln Pro Ser
                 95
```